United States Patent [19]

Codington

[11] Patent Number: 4,837,171

[45] Date of Patent: Jun. 6, 1989

[54] ANTI-EPIGLYCANIN MONOCLONAL ANTIBODIES

[75] Inventor: John F. Codington, West Newton, Mass.

[73] Assignee: The General Hospital Corporation, Boston, Mass.

[21] Appl. No.: 69,311

[22] Filed: Jul. 2, 1987

[51] Int. Cl.⁴ ............................................. G01N 33/53
[52] U.S. Cl. ................................... 436/548; 424/1.1; 424/9; 424/85.8; 424/88; 435/68; 435/172.2; 435/240.26; 435/948; 530/387; 530/402; 530/808; 530/809
[58] Field of Search ................ 424/9, 1.1, 85, 88, 424/93; 435/172.2, 243, 948, 240, 26, 68; 436/548; 530/387, 402, 808, 809

[56] References Cited

U.S. PATENT DOCUMENTS 4,647,447  3/1987  Gries et al. .............................. 424/9

OTHER PUBLICATIONS

Kohler, et al., Nature, vol. 256, (1975), pp. 495–497.
American Type Culture Collection Catalogue of Cell Lines and Hybridomas, Fifth Edition, (1985), pp. 287–293.
Codington et al., 73 J. Nat'l Cancer Inst. 1029 (1984).

Primary Examiner—Robert J. Warden
Assistant Examiner—Stephen C. Wieder

[57] ABSTRACT

Monoclonal antibodies reactive with epiglycanin.

11 Claims, No Drawings

ANTI-EPIGLYCANIN MONOCLONAL ANTIBODIES

BACKGROUND OF THE INVENTION

This invention relates to immunologic diagnosis of malignancy.

Classical methods of screening for cancer have included x-rays, biopsy and physical examination, as well as immunologic methods such as detection of immune complexes formed by antibodies to cancer cells.

Cells of allotransplantable ascites sublines of the strain A mouse TA3 mammary carcinoma cell line express large quantities of epiglycanin on their surface. Mouse epiglycanin consists of a single polypeptide chain of about 1,300 amino acid residues, to which more than 500 carbohydrate chains are attached; carbohydrate represents about 75–80% of the glycoprotein, which has an $M_r 500,000$. Codington et al., 73 J. Natl. Cancer Inst. 1029 (1984) induced anti-epiglycanin polyclonal antibodies by injecting these sublines into rabbit and mouse, and reported the presence in body fluids from human patients, particularly those having metastatic cancer, of glycoprotein that binds to anti-epiglycanin polyclonal antibody.

SUMMARY OF THE INVENTION

In general, the invention features cell lines, and the epiglycanin reactive monoclonal antibodies produced by them. In preferred embodiments the monoclonal antibodies are labeled, and preferably radiolabeled or complexed with a paramagnetic ion to form an NMR contrast agent.

The monoclonal antibodies of the invention can be used in any of several diagnostic methods and diagnostic kits therefor for testing for malignancy in a mammal.

Because of the high specificity of the monoclonal antibodies for particular epitopes on epiglycanin-like polypeptides, and because of the wide variety of malignant cells that express epiglycanin-like polypeptides on their surfaces, the methods can be used for broad screening for malignancies.

The monoclonal antibodies of the invention are produced by hybridomas made by immunizing an animal by injection of a mammal with asialoepiglycanin, and fusing spleen cells from the mouse with myeloma cells.

Other advantages and features of the invention will become apparent from the description of the preferred embodiments and from the claims.

DESCRIPTION OF PREFERRED EMBODIMENTS

The structure, method of preparation, and use of the preferred embodiments of the invention are now described.

Monoclonal Antibodies to Epiglycanin

The monoclonal antibodies of the invention were prepared by procedures based on the technique developed by Kohler and Milstein, 256 Nature 495 (1975). Generally, somatic cell hybrids or hybridomas are formed in a selective medium by fusing cells from a culture of continuously dividing ("immortal") tumor cells with spleen cells or lymph cells harvested from an animal immunized to the chosen epitope; myeloma cells are killed by the selective medium, and splenocytes or lymphocytes eventually die at the end of their natural life span, leaving only the hybridomas. Each hybridoma is an immortal cell line capable of continuously secreting an antibody specific to a single epitope, by maintenance of the cell line in tissue culture or by injection and ascites formation in vivo. For production of monoclonal antibodies to epiglycanin, the chosen epitope is on the epiglycanin molecule. In the preparation of preferred embodiments, mice are immunized by repeated subcutaneous ("sc") or intraperitoneal ("ip") injection of asialoepiglycanin, and spleen cells from each mouse are fused with mouse myeloma cells to form hybridomas. The hybridomas are then cloned and grown in ascites form in mice for monoclonal antibody production. The monoclonal antibodies are then purified by methods known in the art, as reviewed by Goding, Monoclonal Antibodies: Principles and Practice, Academic Press, New York (2nd Edition, 1986).

A more detailed outline of a protocol for obtaining the monoclonal antibodies of preferred embodiments is set out below, but one skilled in the art will recognize that monoclonal antibodies that are within the scope of the invention may be obtained by following protocols differing in particulars from the one presented here.

1. Production and purification of asialoepiglycanin

Mouse tumor cells expressing epiglycanin at their cell surfaces are capable of progressive growth in other mice of the same species (allogeneic hosts) or in animals of other species (xenogeneic hosts), and after a period of such growth, epiglycanin appears in the host's body fluids. In preferred embodiments, ascites cells of the TA3-Ha subline of the strain A mouse TA3 mammary carcinoma, described in Cooper et al., 63 J. Natl. Cancer Inst. 163 (1979), maintained by serial passage in commercially available strain A/WySn mice, were injected (ip) into A/WySn mice, and epiglycanin was isolated from the host ascites fluid 7 days later and purified by column chromatography by techniques described in Cooper et al., id. Sialic acid was removed from the purified epiglycanin by heating a solution of the epiglycanin in 0.05M sulfuric acid at 80° for 60 minutes, and the mixture was dialyzed against hemagglutination buffer, pH 7.0.

2. Preparation and purification of monoclonal antibodies to epiglycanin

The fusion of myeloma and spleen cells that gave the best yield of positive clones, as measured by an enzyme-linked immunosorbent assay ("ELISA"), resulted from multiple injections of a commercially available strain C57BL mouse with asialoepiglycanin and the fusion of spleen cells from this mouse with SP2/0-Ag14 ("SP2"; available from the ATCC) mouse myeloma cells. Immunization with asialoepiglycanin gave an enhanced immune response as compared with immunization with epiglycanin. Four monoclonal antibodies from this fusion, AE-1, AE-2, AE-3 and AE-4, were obtained 90–95 percent pure after precipitation with 50 percent saturated ammonium sulfate, followed by fractionation on a column of Sephadex G-200.

More particularly, antiepiglycanin antibodies were induced in four 6-week-old C57BL female mice by injection (ip) of asialoepiglycanin (50 μg) at days 0, 14, and 21. At days 14 and 21 the immunogen was administered in an emulsion with Freund's complete adjuvant. Mice were bled prior to each injection, and relative antibody titre was compared at weekly intervals for the four injected mice, as well as for a fifth mouse, which was injected concurrently with saline. Hyperimmunization of the mouse with highest titre was performed on day 35, with an injection (ip) of 30 μg of asialoepiglycanin. Fusion with SP2 mouse myeloma cells was performed on day 38. Myeloma cells were removed and hybridomas were cloned, subcloned, grown in culture, and, finally, grown in ascites form in commercially available strain CBYB6F$_1$ mice by methods known in the art and described in, for example, Galfré et al., 73 Methods Enzymol. 3 (1981). As a growth medium for hybridoma cells Dulbecco's Modified Eagle medium with 20 percent Nu serum, high glucose, added glutamine (0.5 g/liter), and penicillin (100 U/Ml) streptomycin (100 μg/ml) was used The monoclonal antibodies were purified by methods known in the art, including generally the following steps: (1) precipitation in 50 percent saturated ammonium sulfate; (2) washing of the pellet with 50 percent saturated ammonium sulfate; and (3) fractionation of the dissolved and dialyzed solution on DEAE cellulose (Sigma), or fractionation of the non-dialyzed solution on a column of Sephadex G-200 (Pharmacia) with 0.20M NaCl, pH 7.5, as eluent.

Isotyping of the antibodies was performed with a mouse immunoglobulin subtype identification kit from Boehringer-Mannheim. The results were checked by polyacrylamide gel electrophoresis with SDS, and the migrations of the heavy chains were compared with standard immunoglobulins.

3. Characteristics of the monoclonal antibodies

Polyacrylamide gel electrophoresis with SDS, in the presence of β-mercaptoethanol, suggested that 90–95 percent of the protein, as determined by Coomassie blue staining, was present in bands migrating with immunoglobulin heavy and light chains. It appeared that at least 95 percent of band intensity in the heavy chain regions was present as the μ chain, suggesting that nearly all of the antibody was of the IgM type. Yields of the monoclonal antibodies ranged from 4–9 mg/ml as determined by their protein contents. The predominance of IgM type antibodies was also indicated by the results of ELISA-type assays with antibodies supplied as a kit by Boehringer-Mannheim. Each of the antibodies gave strong positive readings in the ELISA assay, when wells were initially coated with either epiglycanin or asialoepiglycanin. Two of the four antibodies (AE-3 and AE-4) gave insoluble antigen-antibody complexes in radioimmunoassays ("RIA") utilizing $^{125}$-I-epiglycanin. The slopes of the AE-3 and AE-4 RIA curves were similar to that of a standard curve utilizing rabbit anti-epiglycanin polyclonal antibody, but were about fivefold less sensitive. The inhibition curve for AE-1 exhibited an even steeper slope but possessed a maximum amount of precipitate at only 40 ng.

4. Antigenic determinants

Studies were done to determine the proportion of the inhibitory activity of epiglycanin lost after treatment with periodate or with endo-α-N-acetyl-D-galactosaminidase (prepared from *Diplococcus pneumoniae*). Endo-α-N-acetyl-D-galactosaminidase is capable of cleaving only the disaccharide 2-acetamido-2-deoxy-3-O-β-D-galactopyranosyl-α-D-galactopyranose, which is linked to serine or threonine in epiglycanin. Each of the two treatments was capable of removing the capacity of the antibodies to bind to epiglycanin, suggesting that the epitope is a glycopeptide moeity containing a Galβ1-3GalNAc chain.

Three monoclonal antibodies differ markedly in the extent of inhibition shown in RIA by the immunogen of the T antigen, asialoglycophorin A. The inhibitory activities of asialoglycophorin A in radioimmunoassays utilizing $^{125}$I-epiglycanin and two of the monoclonal antibodies, AE-1 and AE-3, indicate weak binding of these antibodies. The observation that AE-4 binds to asialoglycophorin A approximately as well as it does to epiglycanin strongly suggests that the two glycoproteins, epiglycanin and glycophorin A, possess a common amino acid sequence at the site of the disaccharide chain attachment. AE-1 and AE-3 may require the sequence of amino acids that is required by AE-4, but may recognize additional amino acids as well. The weak binding exhibited by the three monoclonal antibodies to the antifreeze glycoprotein, which possesses multiple carbohydrate chains of the same structure as the epiglycanin disaccharide, suggests that the binding sites for these antibodies require peptide linkages in addition to the carbohydrate chain.

Diagnostic Tests

Each of the diagnostic methods employing monoclonal antibodies to epiglycanin is designed to determine the concentration of immunoreactive epiglycanin-like glycopeptide in the serum of an animal under examination for malignancy. In preferred embodiments, the methods utilize techniques of radioimmune assay of an enzyme-linked immunosorbent assay. In each technique samples at various dilutions of the serum and samples at known dilutions of affinity purified epiglycanin are tested, and the concentration of immunoreactive epiglycanin-like glycopeptide in the serum is determined with reference to a standard curve produced by testing the purified epiglycanin.

A protocol designed to be suitable for practicing the immunodiagnostic methods of the invention follows.

1. Preparation of affinity purified epiglycanin

Epiglycanin is harvested from viable TA3-Ha ascites cells and purified as follows. The cells are incubated for a time in a proteolytic enzyme solution. Then the cells are removed from the solution, for example by centrifugation, and the supernatant recovered and kept cold. Incubation is repeated a number of times in fresh enzyme solution, and the supernatent from each incubation is recovered and kept cold. The pooled supernatants are then clarified by high speed centrifugation, and the clear solution is lyophilized. It is suitable for each incubation to suspend $10^9$ cells in 25 ml of a solution of 18 μg/ml of TPCK-trypsin in PBS and rotate at 0°–4° C. for 30 minutes, and it is suitable to perform three incubations on the cells. Clarification is satisfactorily achieved by centrifugation at 10,000×g for 30 minutes.

The lyophilized solution containing harvested epiglycanin is then fractionated by passing it successively through two sephadex columns and an affinity column. The first column comprises, for example, Sephadex G-10, and removes all salt. The second column comprises, for example, Sephadex G-150, and removes the epiglycanin (average molecular weight 200,000) from other proteins cleaved from the cells during proteolysis. A suitable eluent for the Sephadex columns is 0.10M pyridine acetate at pH 5.3. Material from the first large peak from the second column is then lyophilized and may be stored indefinitely in the cold. Finally, affinity purified epiglycanin is obtained by fractionating this lyophilized material on a wheat germ agglutinin affinity column.

2. Preparation of $^{125}$I-Epiglycanin

Epiglycanin, isolated substantially as described in Codington et al., 63 J. Nat'l Cancer Inst. 153 (1979), from the ascites fluid of strain A mice bearing the TA3-Ha cells in the peritoneal cavity, is iodinated using reshly prepared Bolton-Hunter Reagent, substantially as described in Codington et al., 73 J. Nat'l Cancer Inst. 1029 (1984). The iodinated product is purified, for example, by fractionation on a column of Sepharose 4B.

3. The competitive RIA

The competitive radioimmunoassay for epiglycanin may be carried out as follows. All procedures utilize 0.10M ammonium acetate (pH 7), as solvent. Samples of epiglycanin, for the standard curve, and of unknown serum samples are run simultaneously. The standard curve is made from a series of runs, comprising different concentrations of epiglycanin in buffer. A suitable series may include, e.g., 5-fold dilutions over the concentration range 200 ng/50 µl to 0.064 ng/50 µl, and a run with buffer alone. Unknown samples are tested at dilutions such as 1:2, 1:4, and 1:8 and can be run in duplicate. A suitable protocol for the incubations is as follows. The initial reaction is run with 50 µl of sample and 100 µl of monoclonal antibody (at an appropriate dilution), and incubation proceeds with gentle rocking at 37° C. for 60 minutes and at 4° C. for 60 min. After the addition of 50 µl of $^{125}$I-epiglycanin (2000 CPM/tube) and mixing, the tubes are incubated with gentle rocking at 0°–4° C. for 15 h. Agarose-bound goat anti mouse IgG and IgM in 500 µof solvent is added to the mixture. After incubation of the mixture for 5 hours at 4° C. with gentle rocking, the tubes are centrifuged at about 1000×g for 10 min. The supernatants are removed, and the residues washed two times with 200 µl of solvent. Both the supernatants and the solid residues are counted in a gamma counter. The standard curve consists of a plot of the log of the epiglycanin concentration against the percent of radioactivity in the solid residue. The amount of immunoreactive epiglycanin in unknown samples is then determined with reference to the standard curve.

4. The Competitive ELISA

The competitive enzyme-linked immunosorbent assay may be carried out as follows. Wells of an assay plate are coated with epiglycanin and then the epiglycanin coat is incubated with ovalbumin. Monoclonal antibody to epiglycanin is incubated for a time with samples of purified epiglycanin (for the standard curves) and with serum to be tested for epiglycanin-like glycopeptide, and these mixtures are then incubated for a time with the epiglycanin-ovalbumin in the wells. Then enzyme-conjugated antiserum at an appropriate dilution is added to the wells and allowed to incubate for a time. Then fresh substrate is introduced to the wells and allowed to incubate until the reaction has developed sufficiently in the standard solution. Then the reactions are stopped and the relative enzyme activities are recorded. The wells are washed between incubation steps, and appropriate control wells are prepared for each run, including wells lacking antigen, lacking antibody, lacking enzyme conjugated antibody, and lacking substate.

A 96 well flexible assay plate (0.3 ml/well) is suitable for the ELISA. To coat the wells with epiglycanin, 100 µl of a solution of 200 µg of epiglycanin in 10 ml of 0.10M ammonium acetate (with 0.05% TWeen 20) ("AA-TW") is allowed to stand in the wells at 0°–4° C. for 15–20 hours, after which the solution is removed and the wells washed 4 times with AA-TW. Then 200 µl of 1% ovalbumin in AA-TW is allowed to incubate in each well at 37% C for 2 hours, after which the ovalbumin is discarded and the wells washed 2 times with AA-TW. The prepared assay plates are then covered with parafilm to retain moisture until use.

Each of the prepared wells is then allowed to incubate at 37° C. for 2 hours with 100 µl of a mixture, which had previously been incubated at 37° C. for 2 hours, of 200 µl of a monoclonal antibody to epiglycanin, at an appropriate dilution, and 100 µl of either epiglycanin (for the standard curve) or the samples to be tested. The standard curve is made by using a series of epiglycanin concentrations, such as 5-fold dilutions in the range 200 ng to 0.064 ng; the samples to be tested will be a series of dilutions, e.g., 1:2, 1:4, and 1:8, of serum. After this incubation, the solutions are removed and the wells washed 3 times with 200 µl of AA-TW. Then 200 µl of peroxidase-conjugated antiserum at an appropriate dilution is allowed to incubate in the wells at 37° C. for 90 min., after which the solution is discarded and the wells washed 4 times with 200 µl of AA-TW.

Substrate should be prepared fresh. For peroxidase-conjugated antiserum, as described in this protocol, satisfactory results are obtained with a substrate prepared by mixing a solution of 40 µl of ABTS (2,2'-azino-bis-(3-ethylbenz-thiazolinesulfonic acid)) stock solution (21.9 mg/ml water) in 8 ml of citrate buffer (0.05M, pH 4.0) with 32 µl of $H_2O_2$, within a few minutes before use. To each well is added 100 µl of the substrate mixture, and the reaction is allowed to run at room temperature until an appropriate color has developed in the standard solution. The reaction is stopped by adding 50 µl of a 2.5M hydrofluoric acid solution to each well. Enzyme activity in each well is determined by measuring light absorption at the appropriate wavelength.

Deposits

The following deposits have been made with the American Type Culture Collection (ATCC), 12301 Parkland Drive, Rockville, MD 20852 USA, where the deposits were given the following accession numbers:

| Deposit | Accession No. |
|---------|---------------|
| HAE-1   | HB 9466       |
| HAE-3   | HB-9467       |
| HAE-4   | HB-9468       |

Applicant's assignee, The Massachusetts General Hospital Corporation, represents that the ATCC is a depository affording permanence of the deposit and ready accessability thereto by the public if a patent is granted. All restrictions on the availability to the public of the material so deposited will be irrevocably removed upon the granting of a patent. The material will be available during the pendency of the patent application to one determined by the Commissioner to be entitled thereto under 37 CFR 1.14 and 35 USC 122. The deposited material will be maintained with all the care necessary to keep it viable and uncontaminated for a period of at least five years after the most recent request for the furnishing of a sample of the deposited microorganism, and in any case, for a period of at least thirty (30) years after the date of deposit or for the enforceable life of the patent, whichever period is longer. Applicant's assignee acknowledges its duty to replace the deposit should the depository be unable to furnish a sample when requested due to the condition of the deposit.

Other Embodiments

Other embodiments are within the following claims. For example, labeled monoclonal antibodies of the invention can be used for detecting and locating malignant cells in vivo, particularly in localized tumors. the high binding affinity and specificity of the monoclonal antibodies can provide good sensitivity for malignant cells having epiglycanin-like glycopeptides on their surface.

The monoclonal antibodies can be labeled using any conventional label, e.g., a radiolabel or a fluorophore. To carry out in vivo imaging in the detection and localization of malignant cells, an animal such as a human patient can be given an intravenous injection of, for example, appropriately radiolabeled antibody in physiological saline. Whole body scan scinitigrams can then be taken using a gamma camera interfaced with a computer.

The monoclonal antibodies of the invention can also be labeled with a paramagnetic ion to provide a targeted NMR contrast agent. The paramagnetic ion can be complexed with the monoclonal antibody via a chelating agent using conventional techniques. The contrast agent can be administered to an animal such as a human patient and NMR imaging carried out; the agents will provide NMR contrast between malignant cells, having on their surfaces epiglycanin-like glycopeptides, and other tissues.

I claim:

1. A hybridoma cell line deposited in the ATCC and having accession number ATCC HB 9466.
2. A hybridoma cell line deposited in the ATCC and having accession number ATCC HB 9467.
3. A hybridoma cell line deposited in the ATCC and having accession number ATCC HB 9468.
4. The monoclonal antibody produced by the cell line of claim 1.
5. The monoclonal antibody produced by the cell line of claim 2.
6. The monoclonal antibody produced by the cell line of claim 3.
7. The antibody of any claims 4, 5, or 6, said antibody being labeled.
8. The antibody of claim 7, said antibody being radiolabeled.
9. The antibody of claim 7, said antibody being complexed with a paramagnetic ion to form an NMR contrast agent.
10. A monoclonal antibody recognizing epiglycanin glycopeptide selected from the group consisting of AE-1, AE-3, and AE-4.
11. An antibody producing hybridoma cell capable of producing monoclonal antibodies recognizing epiglycanin glycopeptide selected from the group consisting of HAE-1, HAE-3, and HAE-4.

* * * * *

UNITED STATES PATENT AND TRADEMARK OFFICE
CERTIFICATE OF CORRECTION

PATENT NO. : 4,837,171

DATED : June 6, 1989

INVENTOR(S) : JOHN F. CODINGTON

It is certified that error appears in the above-identified patent and that said Letters Patent is hereby corrected as shown below:

Column 1, line 1, add the following:

--This invention was made with government support under 7R01CA43060-01 and CA08418 awarded by the National Cancer Institute of the National Institutes of Health. The government has certain rights in the invention.--

Signed and Sealed this

Twenty-second Day of September, 1992

Attest:

DOUGLAS B. COMER

Attesting Officer

Acting Commissioner of Patents and Trademarks